United States Patent
Vanden Eynde et al.

(10) Patent No.: US 11,225,451 B2
(45) Date of Patent: Jan. 18, 2022

(54) PROCESS FOR THE PREPARATION OF 3,3,4-TRIMETHYLCYCLOHEXYLIDENE BISPHENOL (BP-TMC)

(71) Applicant: Covestro Intellectual Property GmbH & Co. KG, Leverkusen (DE)

(72) Inventors: Johan Vanden Eynde, Zwijnaarde (BE); Kristof Heylen, Zemst (BE); Anja Ehrig, Leverkusen (DE); Lars Frye, Leichlingen (DE)

(73) Assignee: Covestro Intellectual Property GMBH & Co. KG, Leverkusen (DE)

( * ) Notice: Subject to any disclaimer, the term of this patent is extended or adjusted under 35 U.S.C. 154(b) by 0 days.

(21) Appl. No.: 17/288,309

(22) PCT Filed: Nov. 13, 2019

(86) PCT No.: PCT/EP2019/081106
§ 371 (c)(1),
(2) Date: Apr. 23, 2021

(87) PCT Pub. No.: WO2020/108989
PCT Pub. Date: Jun. 4, 2020

(65) Prior Publication Data
US 2021/0371365 A1  Dec. 2, 2021

(30) Foreign Application Priority Data

Nov. 26, 2018 (EP) .................................. 18208309
Dec. 6, 2018 (LU) .................................. LU101025

(51) Int. Cl.
C07C 37/20 (2006.01)
C07C 37/82 (2006.01)
C07C 37/84 (2006.01)
C07C 37/68 (2006.01)

(52) U.S. Cl.
CPC ............ *C07C 37/20* (2013.01); *C07C 37/685* (2013.01); *C07C 37/82* (2013.01); *C07C 37/84* (2013.01)

(58) Field of Classification Search
CPC ............. C07C 37/002; C07C 2601/14; C07C 2601/16
See application file for complete search history.

(56) References Cited

U.S. PATENT DOCUMENTS

| 5,648,561 A | 7/1997 | Tan et al. |
| 6,858,758 B2 * | 2/2005 | Van Osselaer .......... C07C 37/16 568/728 |
| 2003/0050514 A1 | 3/2003 | Osselaer et al. |
| 2005/0165258 A1 | 7/2005 | Yao et al. |

FOREIGN PATENT DOCUMENTS

| EP | 0995737 A1 * | 4/2000 | ............ C08G 75/23 |
| EP | 1318132 A1 | 6/2003 | |

OTHER PUBLICATIONS

International Search Report for International Patent Application No. PCT/EP2019/081106, dated Jan. 15, 2020.
Written Opinion for International Patent Application No. PCT/EP2019/081106, dated Jan. 15, 2020.

* cited by examiner

*Primary Examiner* — Sikarl A Witherspoon
(74) *Attorney, Agent, or Firm* — K&L Gates LLP

(57) ABSTRACT

The present inventions relates to the preparation of 3,3,5-trimethylcyclohexylidene bisphenol. Especially, the present invention relates to the preparation of 3,3,5-trimethylcyclohexylidene bisphenol from 3,3,5-trimethylcyclohexanone and phenol in the presence of a gaseous acidic catalyst. The preparation comprises a first drying step and a second drying step wherein in the second drying step the temperature is increased in comparison to first drying step or in the second drying step the pressure is lowered in comparison to first drying step, or in second drying step both the temperature is increased and the pressure is lowered in comparison to the first drying step (d1).

20 Claims, No Drawings

PROCESS FOR THE PREPARATION OF 3,3,4-TRIMETHYLCYCLOHEXYLIDENE BISPHENOL (BP-TMC)

CROSS REFERENCE TO RELATED APPLICATIONS

This application is a U.S. national stage application, filed under 35 U.S.C. § 371, of International Application No. PCT/EP2019/081106, which was filed on Nov. 13, 2019, and which claims priority to Luxembourg Patent Application No. LU101025, which was filed on Dec. 6, 2018 and European Patent Application No. 18208309.7, which was filed on Nov. 26, 2018. The contents of each are hereby incorporated by reference into this specification.

FIELD

The present inventions relates to the preparation of 3,3,5-trimethylcyclohexylidene bisphenol. Especially, the present invention relates to the preparation of 3,3,5-trimethylcyclohexylidene bisphenol from 3,3,5-trimethylcyclohexanone and phenol in the presence of a gaseous acidic catalyst. The preparation comprises a first drying step and a second drying step wherein in the second drying step the temperature is increased in comparison to first drying step or in the second drying step the pressure is lowered in comparison to first drying step, or in second drying step both the temperature is increased and the pressure is lowered in comparison to the first drying step (d1).

BACKGROUND

The preparation of 3,3,5-trimethylcyclohexylidene bisphenol, hereinafter also referred to as BP-TMC, from 3,3,5-trimethylcyclohexanone, hereinafter referred to as TMC-one, as a first reactant and phenol as a second reactant in a reaction vessel in the presence of a gaseous acidic catalyst is known per se.

Basically the reaction proceeds as follows according to Scheme 1:

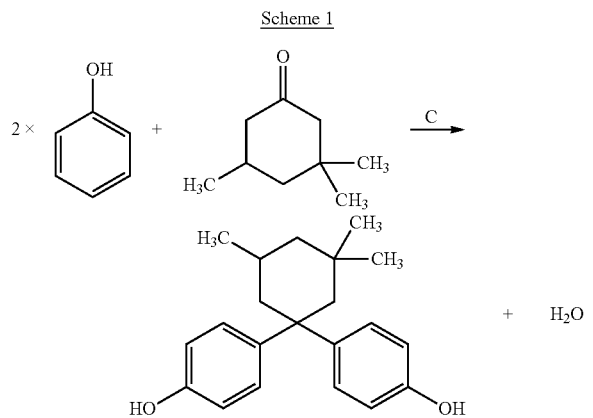

EP0995737A1 discloses the preparation of BP-TMC from TMC and phenol in the presence of acidic catalyst already. EP0995737A1 also mentions that the obtained reaction product is dried but does not disclose any details thereto.

EP1277723A1 also discloses the preparation of BP-TMC from TMC and phenol in the presence of acidic catalyst already, too. Also EP1277723A1 mentions that the obtained reaction product is dried. However, EP1277723A1 does not disclose any details to the drying of the reaction product either.

According to EP1277723A1 BP-TMC can be obtained as crystals of an BP-TMC-phenol-adduct intermittent. The content of EP1277723A1 is incorporated into the present description by reference.

In an industrial process for the production of BP-TMC these crystals comprise from 60 to 70 wt.-% of BP-TMC and from 30 to 40 wt.-% of phenol; these crystals also may comprise inevitable impurities in a very low amount, especially less than 1000 ppm. These inevitable impurities are introduced by the reactants and catalysts, e.g. One skilled in the art knows the types and amounts of all major inevitable impurities. BP-TMC then is obtained as crystals comprising at least 99 wt.-%, preferably at least 99.5 wt.-%, most preferably at least 99.9 wt.-% of BP-TMC and less than or equal to 1000 ppm, preferably less than or equal to 300 ppm, most preferably less than or equal to 200 ppm of phenol by drying. The amount of BP-TMC plus the amount of phenol plus the amount of inevitable impurities sums up to 100 wt.-% always. During drying the phenol is evaporated.

However, the melting point of pure BP-TMC at atmospheric pressure (1013.25 mbar) is 210° C. and the thermal stability of BP-TMC requires drying temperatures lower than 200° C. to avoid that the BP-TMC is degraded during drying. The degradation of BP-TMC causes a final product with more impurities and of poor crystal structure which is difficult to transport and to use in an further process, e.g. the preparation of a polycarbonate using BP-TMC and phosgene in a phase boundary process or using BP-TMC in a melt transesterification using diphenyl carbonate.

Therefore it is not possible to keep a whole setting up comprising crystals comprising BP-TMC obtained in an industrial process for the production of BP-TMC in liquid state during drying. The phenol content of the crystals is reduced during drying. Technically it is desired to keep the whole setting up comprising crystals comprising BP-TMC in liquid state during drying since this would enhance the drying, especially it would accelerate the drying. However, this is not possible for the reasons explained above. Therefore it is required to conduct the drying of the crystals comprising BP-TMC in a solid state in a dryer. During drying in a conventional dryer, e.g. a rotary dryer, the problem occurs that due to the high amount of phenol—coming from the evaporation from the crystals of the BP-TMC-phenol-adduct—in the inner volume of the dryer the input of thermal energy has to be very high to keep the temperature high enough to achieve a reasonable evaporation of the phenol from the crystals of the BP-TMC-phenol-adduct. This in turn leads to the situation that the temperature of inner walls of the dryer has to be so high that the crystals comprising BP-TMC which are in contact with the inner walls of the dryer become liquid. This leads again to morphology changes of the crystals, i.e. poor crystal structure, or even to degradation of BP-TMC.

Since 2,2-Bis(4-hydroxyphenyl)propan (bisphenol A, BPA) has a lower melting point (about 155° C.) at atmospheric pressure (1013.25 mbar) there is not the problem of decomposition when BPA is converted into the liquid state. Therefore the methods for drying BPA cannot be used for drying BP-TMC.

To overcome the above explained problems according to the state of the art batch dryers are used for the drying setting up comprising crystals comprising BP-TMC. These batch dryers change the temperature over time and can thus avoid this issue. Batch dryers are however more expensive to operate since they do not work continuously resulting in large buffer volumes and they ask for additional manipulation steps.

Another solution according to the state of the art, e.g. EP 1318132 A1, is to use a solvent in a recrystallization step that is not mixable with phenol and BP-TMC. This will remove the phenol from the adduct and form BPTMC crystals in such a solvent. As these BP-TMC crystals are no longer part of an adduct between BP-TMC and phenol, the melting point of these crystals are much higher resulting into no phase change of the crystals due to the temperature increase required for removal of such a solvent. It will however also result into traces of this solvent to be found in the end product. These traces of the solvent are adverse since they may e.g. disturb the preparation of a polycarbonate resulting from BP-TMC and phosgene or resulting from BP-TMC and diphenyl carbonate.

It is also possible to use a water washing step to remove the phenol from the adduct and remove the water in a drying step. However there will be a high amount of water consumption required to be able to remove the required phenol and a substantial higher energy consumption to evaporate the water.

So, currently it is not possible to conduct drying in a continuous solid drying process to obtain BP-TMC crystals with low content of phenol, especially with a phenol content of less than 1000 ppm, preferably of less than 300 ppm, most preferably of less than 200 ppm.

SUMMARY

Therefore it is an object of the present invention to overcome the disadvantages of the state of the art.

Especially it is an object of the invention to provide a process for preparing BP-TMC with a purity of at least 99 wt.-%, the process comprising continuously conducted drying steps.

Surprisingly the object was achieved by the subject matter of claim 1. Preferred embodiments can be found in the dependent claims.

Especially the object was achieved by:

A process for preparing BP-TMC comprising less than 1000 ppm of phenol, the process comprising the steps of:
(a) reacting TMC-one and phenol in the presence of an acidic catalyst to give a product mixture comprising BP-TMC in the form of an BP-TMC-phenol-adduct and water,
(b) separating the BP-TMC-phenol-adduct from the product mixture,
wherein the process further comprises the steps of:
(d) removing the phenol from the BP-TMC-phenol-adduct by
(d1) drying the BP-TMC-phenol-adduct at a temperature of less than or equal to 160° C., more preferably less than or equal to 145° C. and an absolute pressure of from 200 mbar to 20 mbar, preferably from 50 to 25 mbar, until an intermediate product mixture comprising BP-TMC-phenol-adduct and BP-TMC is obtained, this intermediate product mixture having a phenol concentration below 10 wt.-%, and
(d2) drying the intermediate product mixture obtained from step (d1) at a temperature from 150° C. to 180° C. and an absolute pressure of less than 50 mbar, preferably less than 25 mbar, more preferably less than 20 mbar, wherein in step (d2) the temperature is increased in comparison to step (d1) or in step (d2) the pressure is lowered in comparison to step (d1), or in in step (d2) both the temperature is increased and the pressure is lowered in comparison to step (d1).

DETAILED DESCRIPTION

In step (d1) the initial phenol concentration of the crystals is at least 50 wt.-% and then is reduced to a value of below 10 wt.-%.

Preferably in step (d1) the temperature is higher than or equal to 135° C. and less than or equal to 160° C., more preferably higher than or equal to 135° C. and less than or equal to 145° C.

Preferably in step (d2) the temperature is at least 20° C. higher than in step (d1).

Further preferably in step (d2) the pressure is at least 10 mbar lower than in step (d1).

Further preferably in step (b) the BP-TMC-phenol-adduct is obtained as crystals comprising BP-TMC and phenol.

After the completion of step (d) the BP-TMC is obtained as crystals.

Further preferably at least one of steps (d1) or (d2) is conducted in a rotary dryer.

Further preferably the phenol is removed from the BP-TMC-phenol-adduct crystals in absence of any organic solvent except phenol.

Further preferably neither the BP-TMC-phenol-adduct nor the BP-TMC are molten during steps (d1) or (d2), i.e. that both the BP-TMC-phenol-adduct and the BP-TMC are crystals during steps (d1) or (d2).

Further preferably the BP-TMC obtained in step (d2) has a phenol content of less than 1000 ppm, preferably less 300 ppm, more preferably less than 200 ppm, most preferably less than 150 ppm.

Further preferably steps (d1) and (d2) are performed continuously.

Further preferably in step (d1) the phenol concentration of the crystals is reduced to below 5 wt.-%.

Further preferably in step (a) the gaseous acidic catalyst comprises hydrogen chloride and hydrogen sulfide. Preferably the gaseous acidic catalyst is a mixture of hydrogen chloride and hydrogen sulfide.

Further preferably in step (b) the BP-TMC-phenol-adduct is separated by
(b1) removing the catalyst and the water by distillation,
(b2) crystallizing the BP-TMC-phenol-adduct from the distillation residue, and
(b3) separating the BP-TMC-phenol-adduct by filtration.

Further preferably the process further comprising the step of
(c) recrystallizing the BP-TMC-phenol-adduct crystals obtained in step (b) from liquid phenol.

Further preferably an amount of 20 to 60 wt.-%, preferably 30 to 50 wt.-% of the 3,3,5-trimethylcyclohexylidene bisphenol obtained in step (d2) is conducted back to step (d1).

The process according to the invention provides a BP-TMC with a purity of at least 99 wt.-% having a phenol content of less than 1000 ppm, preferably of less than 300 ppm, most preferably of less than 200 ppm. Due to the fact that neither the BP-TMC-phenol-adduct nor the BP-TMC are molten neither morphology changes in the crystals occur nor degradation of BP-TMC. The crystals obtained by the process according to the invention exhibit a good crystal structure, too. So the BP-TMC can be used for the preparation of polycarbonates without further preprocessing.

What is claimed is:

1. A process for preparing 3,3,5-trimethylcyclohexylidene bisphenol comprising less than 1000 ppm of phenol, the process comprising the steps of:
   (a) reacting 3,3,5-trimethylcyclohexanone and phenol in the presence of an acidic catalyst to give a product mixture comprising 3,3,5-trimethylcyclohexylidene-bisphenol in the form of an 3,3,5-trimethylcyclohexylidene-bisphenol-phenol-adduct and water,
   (b) separating the 3,3,5-trimethylcyclohexylidene-bisphenolphenol-adduct from the product mixture,
   wherein the process further comprises the steps of:
   (d) removing the phenol from the 3,3,5-trimethylcyclohexylidene-bisphenol-phenol-adduct by
      (d1) drying the 3,3,5-trimethylcyclohexylidene-bisphenol-phenol-adduct at a temperature of less than or equal to 160° C. and an absolute pressure of from 200 mbar to 20 mbar until an intermediate product mixture comprising 3,3,5-trimethylcyclohexylidene-bisphenol-phenol-adduct and 3,3,5-trimethylcyclohexylidene-bisphenol is obtained, this intermediate product mixture having a phenol concentration below 10 wt.-%, and
      (d2) drying the intermediate product mixture obtained from step (d1) at a temperature from 150° C. to 180° C. and an absolute pressure of less than 50 mbar wherein in step (d2) the temperature is increased in comparison to step (d1) or in step (d2) the pressure is lowered in comparison to step (d1), or in in step (d2) both the temperature is increased and the pressure is lowered in comparison to step (d1).

2. The process of claim 1, wherein in step (d2) the temperature is at least 20° C. higher than in step (d1).

3. The process of claim 1, wherein in step (d2) the pressure is at least 10 mbar lower than in step (d1).

4. The process of claim 1, wherein in step (b) the 3,3,5-trimethylcyclohexylidene-bisphenol-phenol-adduct is obtained as crystals comprising 3,3,5-trimethylcyclohexylidene bisphenol and phenol.

5. The process of claim 1, wherein at least one of steps (d1) or (d2) is conducted in a rotary dryer.

6. The process of claim 1, wherein the phenol is removed from the 3,3,5-trimethylcyclohexylidene-bisphenol-phenol-adduct crystals in absence of any organic solvent except phenol.

7. The process of claim 1, wherein neither the 3,3,5-trimethylcyclohexylidene-bisphenol-phenol-adduct nor the 3,3,5-trimethylcyclohexylidene bisphenol are molten during steps (d1) or (d2).

8. The process of claim 1, wherein the 3,3,5-trimethylcyclohexylidene bisphenol obtained in step (d2) has a phenol content of less than 1000 ppm.

9. The process of claim 1, wherein steps (d1) and (d2) are performed continuously.

10. The process of claim 1, wherein in step (d1) the phenol concentration of the crystals is reduced to below 5 wt.-%.

11. The process of claim 1, wherein in step (b) the 3,3,5-trimethylcyclohexylidene-bisphenol-phenol-adduct is separated by
   (b1) removing the catalyst and the water by distillation,
   (b2) crystallizing the 3,3,5-trimethylcyclohexylidene-bisphenol-phenol-adduct from the distillation residue, and
   (b3) separating the 3,3,5-trimethylcyclohexylidene-bisphenol-phenol-adduct by filtration.

12. The process of claim 1, wherein the process further comprising the step of
   (c) recrystallizing the 3,3,5-trimethylcyclohexylidene-bisphenol-phenol-adduct crystals obtained in step (b) from liquid phenol.

13. The process of claim 1, wherein an amount of 20 to 60 wt.-% of the 3,3,5-trimethylcyclohexylidene bisphenol obtained in step (d2) is conducted back to step (d1).

14. The process of claim 1, wherein in step (d1) the temperature is higher than or equal to 135° C. and less than or equal to 160° C.

15. A process according to claim 1, wherein in step (d1) the drying the 3,3,5-trimethylcyclohexylidene-bisphenol-phenol-adduct is at a temperature less than or equal to 145° C.

16. A process according to claim 1, wherein in step (d1) the drying the 3,3,5-trimethylcyclohexylidene-bisphenol-phenol-adduct is at a pressure in a range of 50 to 25 mbar.

17. A process according to claim 1, wherein in step (d2) the drying the intermediate product mixture obtained from step (d1) is at a pressure of less than 20 mbar.

18. A process according to claim 1, wherein the 3,3,5-trimethylcyclohexylidene bisphenol obtained in step (d2) has a phenol content of less than 150 ppm.

19. A process according to claim 1, wherein an amount of 30 to 50 wt % of the 3,3,5-trimethylcyclohexylidene bisphenol obtained in step (d2) is conducted back to step (d1).

20. A process according to claim 1, wherein in step (d1) the temperature is greater than or equal to 135° C. and less than or equal to 145° C.

* * * * *